US009597482B2

(12) United States Patent
Hann

(10) Patent No.: US 9,597,482 B2
(45) Date of Patent: *Mar. 21, 2017

(54) APPARATUS AND METHOD FOR MONITORING CATHETER INSERTION

(71) Applicant: Lenn R. Hann, Wheaton, IL (US)

(72) Inventor: Lenn R. Hann, Wheaton, IL (US)

(73) Assignee: Smart IV LLC, Wheaton, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/168,902

(22) Filed: Jan. 30, 2014

(65) Prior Publication Data

US 2014/0171770 A1 Jun. 19, 2014

Related U.S. Application Data

(63) Continuation-in-part of application No. 13/526,303, filed on Jun. 18, 2012, now Pat. No. 8,700,133.

(51) Int. Cl.
*A61M 5/172* (2006.01)
*A61B 5/00* (2006.01)
*A61B 5/0205* (2006.01)
*A61M 25/06* (2006.01)
*A61B 5/05* (2006.01)
(Continued)

(52) U.S. Cl.
CPC .......... *A61M 25/0606* (2013.01); *A61B 5/00* (2013.01); *A61B 5/0205* (2013.01); *A61B 5/05* (2013.01); *A61B 5/6832* (2013.01); *A61M 5/158* (2013.01); *A61B 5/02427* (2013.01); *A61B 5/053* (2013.01); *A61B 5/14552* (2013.01); *A61M 5/16836* (2013.01); *A61M 2005/1588* (2013.01); *A61M 2205/18* (2013.01);
(Continued)

(58) Field of Classification Search
None
See application file for complete search history.

(56) References Cited

U.S. PATENT DOCUMENTS 4,277,227 A 7/1981 Jenkins
4,457,751 A 7/1984 Rodler
(Continued)

FOREIGN PATENT DOCUMENTS

EP 1 205 156 A2 5/2002
ES 2 143 424 5/2000
(Continued)

OTHER PUBLICATIONS http://www.sciencedirect.com/science/article/pii/S0924424703006599, K. Toitsua et al., "Three-axis magneto-impedance effect sensor system for detecting position and orientation of catheter tip," Sensors and Actuators A, 2004, Mar. 15, vol. 111, Issues 2-3 (Abstract Only).

(Continued)

*Primary Examiner* — Long V Le
*Assistant Examiner* — Kevin Pontius
(74) *Attorney, Agent, or Firm* — Pauley Erickson & Kottis

(57) ABSTRACT

A method and apparatus for inserting and monitoring the placement of a cannula tip within a peripheral vein of a human body where the cannula includes a sensor located at predetermined location and mounted on the cannula for sensing the biological material of the body to guide the insertion of the cannula tip into the vein and alerts to the withdrawal of the cannula tip from the vein in the body.

18 Claims, 8 Drawing Sheets

(51) Int. Cl.
*A61M 5/158* (2006.01)
*A61B 5/1455* (2006.01)
*A61B 5/024* (2006.01)
*A61B 5/053* (2006.01)
*A61M 5/168* (2006.01)

(52) U.S. Cl.
CPC ............... *A61M 2205/3317* (2013.01); *A61M 2205/507* (2013.01)

(56) References Cited

U.S. PATENT DOCUMENTS

| | | | |
|---|---|---|---|
| 4,534,756 A | | 8/1985 | Nelson |
| 4,587,975 A | | 5/1986 | Salo et al. |
| 4,647,281 A | | 3/1987 | Carr |
| 4,648,869 A | | 3/1987 | Bobo, Jr. |
| 4,852,580 A | | 8/1989 | Wood |
| 4,877,034 A | * | 10/1989 | Atkins et al. ................. 600/475 |
| 4,899,759 A | | 2/1990 | Pederson et al. |
| 5,092,339 A | | 3/1992 | Geddes et al. |
| 5,109,870 A | | 5/1992 | Silny et al. |
| 5,334,141 A | | 8/1994 | Carr et al. |
| 5,335,668 A | | 8/1994 | Nardella |
| 5,423,743 A | | 6/1995 | Butterfield |
| 5,447,529 A | | 9/1995 | Marchlinski et al. |
| 5,553,611 A | | 9/1996 | Budd et al. |
| 5,603,333 A | | 2/1997 | Konings |
| 5,827,192 A | | 10/1998 | Gopakumaran et al. |
| 5,944,022 A | | 8/1999 | Nardella et al. |
| 5,947,910 A | | 9/1999 | Zimmet |
| 5,954,668 A | | 9/1999 | Uber, III et al. |
| 5,964,703 A | | 10/1999 | Goodman et al. |
| 5,995,208 A | | 11/1999 | Sarge et al. |
| 6,304,776 B1 | | 10/2001 | Muntermann |
| 6,332,870 B1 | | 12/2001 | Van Den Berg |
| 6,337,994 B1 | | 1/2002 | Stoianovici et al. |
| 6,360,123 B1 | | 3/2002 | Kimchi et al. |
| 6,375,624 B1 | | 4/2002 | Uber, III et al. |
| 6,408,204 B1 | | 6/2002 | Hirschman |
| RE37,954 E | | 1/2003 | Sato et al. |
| 6,569,160 B1 | | 5/2003 | Goldin et al. |
| 6,603,997 B2 | | 8/2003 | Doody |
| 6,780,182 B2 | | 8/2004 | Bowman et al. |
| 6,845,264 B1 | | 1/2005 | Skladnev et al. |
| 6,847,841 B1 | | 1/2005 | El Hatw |
| 6,882,879 B2 | | 4/2005 | Rock |
| 7,039,458 B2 | | 5/2006 | Ueda et al. |
| 7,121,150 B2 | | 10/2006 | Krivitski et al. |
| 7,169,107 B2 | | 1/2007 | Jersey-Willuhn et al. |
| 7,454,244 B2 | | 11/2008 | Kassab et al. |
| 7,512,433 B2 | | 3/2009 | Bernhart et al. |
| 7,546,776 B2 | | 6/2009 | Ono |
| 8,078,261 B2 | | 12/2011 | Imam |
| 8,233,957 B2 | | 7/2012 | Merz et al. |
| 8,574,704 B2 | * | 11/2013 | Smith et al. ................. 428/143 |
| 8,628,473 B2 | | 1/2014 | Sliwa et al. |
| 2003/0125774 A1 | | 7/2003 | Salo |
| 2003/0195454 A1 | | 10/2003 | Wariar et al. |
| 2005/0119660 A1 | | 6/2005 | Bourlion et al. |
| 2005/0215945 A1 | | 9/2005 | Harris et al. |
| 2005/0240093 A1 | | 10/2005 | DeArmond |
| 2006/0173251 A1 | | 8/2006 | Govari et al. |
| 2006/0173521 A1 | | 8/2006 | Pond, Jr. et al. |
| 2007/0016007 A1 | | 1/2007 | Govari et al. |
| 2007/0255270 A1 | | 11/2007 | Carney |
| 2008/0009711 A1 | | 1/2008 | Govari et al. |
| 2008/0200828 A1 | | 8/2008 | Abboud et al. |
| 2008/0249467 A1 | * | 10/2008 | Burnett et al. ................. 604/117 |
| 2008/0255470 A1 | | 10/2008 | Hauck et al. |
| 2008/0312521 A1 | | 12/2008 | Solomon |
| 2009/0270695 A1 | | 10/2009 | Mceowen |
| 2010/0041984 A1 | | 2/2010 | Shapland et al. |
| 2011/0106052 A1 | * | 5/2011 | Chiang et al. ................. 604/512 |
| 2013/0338480 A1 | | 12/2013 | Hann |

FOREIGN PATENT DOCUMENTS

| | | |
|---|---|---|
| GB | 2 404 255 B | 1/2005 |
| TW | 200845947 | 1/2008 |
| WO | WO 82/00581 | 3/1982 |
| WO | WO 98/35611 | 8/1998 |
| WO | WO 2007/032665 A2 | 3/2007 |
| WO | WO 2008/090485 A1 | 7/2008 |
| WO | WO 2012/040630 A1 | 3/2012 |

OTHER PUBLICATIONS http://ieeexplore.ieee.org/xpls/abs_all.jsp?arnumber=4122258&tag=1, R. Newbower et al., "Sensor for Catheter-Based Measurements of Electrical Conductivity," Biomedical Engineering, IEEE Transactions on, Feb. 1986, vol. BME-33, Issue: 2 (Abstract Only).

* cited by examiner

APPARATUS AND METHOD FOR MONITORING CATHETER INSERTION

CROSS REFERENCE TO RELATED APPLICATION

This patent application is a continuation-in-part of U.S. patent application Ser. No. 13/526,303, filed on 18 Jun. 2012. The co-pending parent application is hereby incorporated by reference herein in its entirety and is made a part hereof, including but not limited to those portions which specifically appear hereinafter.

BACKGROUND OF THE INVENTION

Field of the Invention

This invention relates to an intravenous apparatus and method, and more particular, to an intelligent intravenous apparatus and method for detecting a problem with a catheter tip placement or withdrawal in and from a vein for infusion of intravenous (IV) fluids.

Discussion of Related Art

Certain emergency circumstances demand immediate intravenous therapy for patients facing life threatening loss of bodily fluids due to accidents or other critical care applications found in emergency centers or in critical care facilities of a hospital. IV therapy requires the infusion of liquid substances directly into a vein of the patient. Typically, IV fluids in a bag suspended from an IV pole employing a drip chamber that is connected to a peripheral IV line which consists of a short catheter inserted through the skin into a peripheral vein outside of the chest or abdomen. This is usually in the form of a cannula-over-needle apparatus, in which a flexible plastic or polymer cannula comes mounted on a metal trocar. Once the tip of the needle and cannula are located properly in the vein, the trocar is withdrawn and discarded. Meanwhile, the cannula is advanced inside the vein to a predetermined position where an external hub or valve area of the catheter is secured to the patient's body by medical tape or the like to hold it in place. Blood is often withdrawn at the time of the initial insertion of the cannula into the patient's vein. This is the most common intravenous access method used in both hospitals and in the field by paramedics or emergency medical technicians (EMTs).

The calibers of cannula generally range from 12 to 26 gauge with 12 being the largest and 26 being the smallest. The part of the catheter remaining outside of the skin is called the IV connecting hub or IV valve that is connected to the IV lines back to the IV hag of fluids. For example, an all-purposes IV cannula for infusions and blood draws might be an 18 and 20 gauge sized cannula manufactured by BD/Becton Dickinson Infusion Therapy AB. This intravenous cannula comes with an inner needle that is removed once the flexible portion of the cannula is fully inserted into the patient's vein.

Due to the different skill levels of the medical personnel inserting the IV cannula into the peripheral vein of a patient's hand or arm, complications sometimes develop in a number of the patients receiving IV fluid therapy from infiltration. This is a condition where through improper insertion or withdrawal of the cannula either into or from a peripheral vein, respectfully, results in IV fluids leaking into the surrounding tissues around the vein causing a potential serious health condition known as infiltration.

Before the blood is withdrawn at the time of insertion, this is also the time to detect whether the cannula portion of the catheter is being properly inserted in the patient's vein or not. If the cannula is not sited properly or the vein is missed or even pierced where the cannula goes through the vein and enters into the surrounding subcutaneous tissue rather than remaining in the vein, complications may develop for the patient receiving the IV fluid therapy. Many serious complications can result from improper cannula insertion into the vein. The potential complications include edema causing tissue damage or may even include necrosis depending on the medication or fluid being infused. This extravasation is a leakage of infused fluids into the vasculature of the subcutaneous tissue surrounding the vein. The leakage of high osmotic solutions or chemotherapy fluids can result in significant tissue destruction or other complications. Therefore, in an emergency room of a hospital where interns or nurses are treating a patient by administering fluids intravenously, it becomes a critical factor in the safety of the patient that IV fluids are indeed flowing into the vein of the patient and not into the surrounding tissue. Insertions of a cannula by EMTs in the field at accident scenes who need to administer IV fluid therapy to an injured party are a critical application where the cannula needs to be inserted properly into the vein and to remain within the vein during transportation to the hospital to prevent a loss of life.

However, due to human error, mistakes are bound to be made while inserting the cannula into a vein or the vein is missed altogether during the initial insertion of the needle/cannula. Other times due to movement of the patient by medical personnel or by the patient themselves, the cannula begins to withdraw from the vein. To avoid this chronic problem or other problems during insertion of the needle through the skin into the vein, the medical staff needs some indication about the successful insertion of the needle and cannula into the patient's peripheral vein. The medical personnel also need a convenient way to monitor and then to be alerted to any withdrawal of the cannula from the vein during IV fluid treatment.

To solve this problem of cannula tip placement and to reduce the incidents of infiltration of IV fluids into the surrounding tissues instead of the vein, the intern, nurse or EMT tasked with the needle insertion into a patient's vein to start the IV therapy would greatly be helped by knowing that their insertion of the cannula into the peripheral vein is being accomplished successfully by some type of feedback signal indicating that the proper insertion of the cannula tip within the vein of a patient has occurred.

To solve the problem of infiltration after the initial insertion of the cannula into the patient's vein when the cannula tube backs out of the vein or begins to leak for various reasons, a variety of complex leak detectors have been proposed for detecting a leak or an extravasation of a liquid injected through a needle into a blood vessel of a human body, as described, for example, in U.S. Pat. Nos. 7,546,776, 6,408,204, 5,964,703, 5,947,910, 6,375,624, 5,954,668, 5,334,141, 4,647,281, and 4,877,034. Still other U.S. Pat. Nos. 6,408,204, 5,964,703, 5,947,910 disclose complex leak detectors for detecting a leaking liquid due to a change in impedance on the skin surface of a human body; U.S. Pat. Nos. 6,375,624, 5,954,668, 5,334,141, 4,647,281 disclose leak detectors for detecting a leaking liquid from a change in temperature of a human organ; and U.S. Pat. Nos. 8,078,261 and 4,877,034 disclose a light-guided catheter and leak detector for placement through the skin and for detecting a leaking liquid from a change in optical characteristics of the blood, respectively. There are a number of various prior art solutions to the infiltration problem that center around the monitoring of the pressures of the IV fluids administered to the patient. The pressure information is used to control the flow of the IV fluids. Examples of pressure monitoring systems are shown in U.S. Pat. Nos. 4,277,227; 4,457,751; 4,534,756; 4,648,869 and 7,169,107.

However, none of these prior art patents teach a highly reliable portable apparatus and method of guiding a catheter into a vein and then detecting the proper insertion of the IV cannula of the catheter during its insertion into the patient's peripheral vein by providing a feedback signal either visual or audible for the intern, nurse or EMT starting the IV therapy. Moreover, this smart IV catheter is highly portable and capable of being used in emergency situations outside of a doctor's office or hospital setting in field emergency situations by EMTs prior to the patient being taken by ambulance to the hospital's emergency room.

Most of these prior art infusion detection systems referred to above while doing a good job in detecting problems once the TV therapy begins, the prior art systems do not monitor the initial insertion of the IV cannula into the vein to make sure the cannula is properly inserted into the patient's vein. Some of the prior art systems even require a substantial infusion of IV liquids prior to even detecting a leakage such as a leakage that occurs when the cannula pulls out of the patient's vein. In short, all of these systems are rather complicated and therefore require expensive pieces of equipment that are not necessarily readily available to paramedics or EMTs in the field who must start the IV therapy to an injured patient at an accident scene or even immediately available to the nurses, interns or EMTs even in a hospital emergency room setting.

SUMMARY OF THE INVENTION

A sharp, pointed rod or trocar fits inside a cannula or the soft catheter tube and the sharp point pierces the skin and is directed into a predetermined vein of the patient by the medical technician or doctor. The trocar is then withdrawn. A sensor generally located within the hollow tubing of the flexible or rigid cannula detects a drop in the impedance as blood flows across the surface of the cannula. The sensor is usually embedded within the polymer material of the cannula that protects it from being damaged when it pierces the skin and enters into the patient's vein. The sensors and the wire connections are generally embedded in the polymer material during the manufacturing and extrusion process or later after the extrusion process the sensors and wire are deposited on the cannula surface and properly covered by a thin skin material to prevent damage or dislocation from the cannula along with any wire connections extending back to a module for processing the sensed signal. The sensor(s) then send an electrical signal back to the module for either a visual display or audible sound indication of proper cannula insertion within the patient's vein. The module may take several shapes and have a predetermined thickness and shape in order to house a power source, processing electronics, a soft button switch or similar device for initiating the device when taken out of its package for the first time to be used on a patient. The processing electronics in the module receives the input signal from the sensor(s) and then generates an output signal that fires a light emitting diode (LED) display or in addition, fires a piezo-electric buzzer horn along with the light indication so the medical technician gets both a light and a sound indication of proper insertion of the cannula into a patient's vein.

In one embodiment, an intravenous catheter for guiding tip placement into a peripheral vein of a body and monitoring any tip removal from the peripheral vein, comprises:

a flexible plastic, tubular cannula having a tip at the distal end for insertion into a peripheral vein of a body and a hub at the opposite end for attachment to an IV bag;

a sensor mounted within the cross section of the cannula at a predetermined location thereon, or at the hub, for sensing an impedance of a sensed biological material in the body including the blood and then generating an output signal representative of a sensed biological material;

processor and modulation circuitry connected to the output signal for receiving and then generating a display or audible sound representing the location of the cannula tip within the biological material being sensed in the body during insertion of the cannula or upon the withdrawal of the cannula from the body; and wherein the display provides a feedback to a physician or medical personnel for correct catheter tip placement in the peripheral vein of the patient and wherein the display provides an alert to shut off the infusate when the tip dislodges from the vein but remains in the body to avoid infiltration into the subcutaneous tissues of the body.

In brilliant sunlight, the sound indicator that varies in sound according to state of properly inserting the cannula into a vein is often more useful to overcome the washed out LED display under brilliant sunlight conditions. In a portable unit of the apparatus, the circuitry to process the signals from the sensor(s), drive the LED display and piezo buzzer are preferably contained within a single application specific integrated chip (ASIC) or other suitable miniaturized circuitry mounted within the module or mounted to the catheter itself.

In another preferred embodiment, the module includes an initiation switch activated when peeling back a suitable protective cover over an adhesive backing to the module used to securely attach the module to the skin of a hand or forearm of the patient once the cannula is properly inserted into the peripheral vein of the patient. Also, a soft or dome switch accessible on the non-adhesive topside of the module could provide multiple functions to be described later in greater detail. This dome switch is also a source for the initial activation of the module and the processing and modulation circuitry when pressed for the first time.

Because of the miniaturization of electronic circuitry today, the module might be integrated or mounted in close proximity to the hub or IV valve on the catheter. The module might also be connected via a wire of predetermined length from the catheter to the module mounted on the hand or forearm of a patient receiving the IV therapy. The signal might even travel either by a wired connection or a wireless connection from the module back to a monitoring station located on either an IV cart, IV pole or other base station located in any predetermined location such as in the patient hospital room, in a hospital emergency room or even in a patient's doctor office. The wireless communication for the device of the present invention includes the use of radio frequencies (RF) like Bluetooth which is a proprietary open wireless technology standard for exchanging data over short distances (using short-wavelength radio transmissions in the ISM band from 2400-2480 MHz) from fixed or mobile devices. This allows a hospital to create personal area networks (PANs) with high levels of security within the hospital where up to seven such devices are capable of being connected to the same base station. Another RF connection available for the device of the present invention is a WiFi connection for a sensing module to receive and then output the processed sensor signal to a potential receiving base station similar to a cellular base station in 3g or 4g communications or Wi-Fi connection. The Wi-Fi technology allows either the sensors or the module to exchange data wirelessly using the radio waves over a computer network, including high-speed Internet connections. Wi-Fi as any wireless local area network (WLAN) product are generally based on the Institute of Electrical and Electronics (IEEE) 802.11 standards. The present invention incorporates both the Bluetooth and WiFi standards in its smart IV Catheter design. These communication networks allow the use of passwords for security purposes.

So the portable IV Catheter/Cannula manufactured according to the present invention includes a multi-functional module that receives signals from the sensors mounted within or on the surface of the cannula and then sends the sensor signals as an input to the sensing module for processing or the sensor signals are sent back to a base station via a hardwired connection or wireless connections of either a Bluetooth or a WiFi connection for processing and displaying the outcome. The electronic circuitry within the sensing module or within the base station then processes the sensor signals for generating output signals to drive the LED display or piezo buzzer for indicating the successful insertion of the cannula into the patient's peripheral vein.

The LED is preferably capable of indicating at least several states. When the needle is first being inserted into the skin, the LED would display a flashing red color that progresses to a steady red as the cannula is inserted further under the skin. As the cannula progresses under the skin to the surface of the vein, a flashing yellow would be seen before the flashing yellow changed to a steady yellow. Finally, the steady yellow would change to a flashing green and then a steady green light when the cannula is fully inserted into the vein and all of the sensors detect the flow of blood within the vein. The changes of colors are directly correlated to the drop in impedance as the sensors located within or on the surface of the cannula sense the condition of a blood flow in the vein. If the cannula is not properly inserted within the vein, the EMT will see a red or flashing red indication from the LED and/or a beeping sound from the Piezo Buzzer related to a pattern of sounds to indicate that it is not properly inserted within the vein.

Once the doctor, intern, nurse or EMT has properly inserted the cannula within the vein, the display of LED or sound from the Piezo Buzzer provides predetermined signals from light or sound that indicate that the cannula is sited properly within the vein. The indication may be on the module unit and/or patch attached to the hand or forearm and/or on a display back at the base station located at the IV pole or other area in proximity to the doctor, intern, nurse or EMT personnel inserting the IV cannula into the patient's peripheral vein. The signal indications are used to properly guide the hand of the caretaker or medical professional to make sure the IV cannula is inserted within the vein of the patient and not into the subcutaneous tissue surrounding the vein. The signals from the sensor(s) spaced a predetermined distance apart from one another which are located within the wall or on surface of the flexible polymer cannula tube along its longitudinal axis from its distal end to generally in close proximity to the end connected to the hub of the cannula show the change of impedance as the cannula is positioned within the vein. The sensors detect the presence or absence of the blood in and around the cannula inserted within the vein at each sensor stage. For example, if the cannula has four sensors A, B, C and D, then we would have at least three sensing stages as follows: A-B, B-C and C-D.

Circuitry within the sensing module processes and modulates the signal(s) from the cannula tube sensors and provide a drive signal to at least one LED located on the module that enables the LED to change between steady red, yellow and green colors or between flashing red, yellow or green colors related to the positioning of the cannula either in or out of the patient's vein. The drive signal could also go to a control panel display or the like at the IV pole etc. or some other base station that could have separate LEDs for the colors of red, yellow and green. A red color at each LED on a control panel display might indicate the absence of blood in proximity to any one of the sensor(s) while a change in color to yellow and then to a solid green color for the LED indicator would indicate the presence of blood being sensed at each sensor stage on the cannula, which in turn indicates a proper insertion of the cannula within the patient's vein. The single or multiple LEDs are arranged in any logical pattern desired on the main control panel or display back at the base station.

In a typical embodiment of the invention, a cannula tube includes at least four sensors spaced apart a predetermined distance from each other. Each sensor is embedded within the sidewall of the flexible polymer cannula tubing. Each sensor is spaced around the circumference of the generally tubular shaped cannula by approximately a 90 degrees rotational change between the first sensor at the distal end to the second sensor etc. such until a full 360 degrees change is reached from the distal end toward the hub end in the spacing of the sensors within the tubing. The first LED at the distal end shows a red signal as the blood is beginning to approach the sensor then it would start changing colors from red to finally green indicating a blood flow across all four sensors and three stages of impedance level of the blood. Likewise, as the blood begins to flow between the sensors the resistance and/or impedance keeps dropping until the blood is across all four sensors and the LED has changed to a solid green with the lowest resistance or impedance level in all three stages. The doctor, intern, nurse or EMT would then see the display change from red to yellow to green with the LED display on the module or on a control panel display providing information on whether the cannula tubing of the IV catheter is properly inserted into the patient's vein as all four sensors are now detecting blood and the impedance is at the lowest reading.

Next, the four sensors are capable of being connected by thin wires or ribbon conductors embedded within the soft plastic wall of the cannula tube leading back to the hub of the catheter and then onto the module located on a forearm or back to a control panel at the base station. The module and the control panel are both capable of housing the electronic circuitry for processing the signals from the sensor(s) and then generating a drive signal for changing the LED color on the module or for selecting the correct colored LED on the control panel located at the IV pole, IV Cart or other medical monitoring panel. The electronic circuitry is also capable of generating a drive signal to an audible alarm. The audible alarm with varying tones provides a means for the healthcare professional inserting the catheter into the patient's vein to be guided during insertion of the cannula within the vein and to further indicate the status of a proper insertion of the cannula within the vein. The electronics required to process the signals and provide the output signal for the LED, LEDs or sound device are capable of being placed within a single ASIC or another miniaturized integrated chip circuitry as shown in U.S. Pat. No. 7,169,107 which is incorporated by reference thereto or other similar miniaturized electronic integrated chip sets which a person having ordinary skill in the medical arts of monitoring patients is capable of assembling.

A method of inserting and monitoring the placement of a catheter tip within a peripheral vein on a patient body according to a preferred embodiment may include: inserting a cannula-over-needle apparatus into the body, the apparatus including a cannula connected to an IV bag at a hub opposite a cannula tip; sensing various biological material within the body from detection circuitry connected to a sensor mounted on the cannula or at the hub; guiding the tip of the cannula corresponding to the sensed biological material; stopping the insertion of the cannula into the body when the sensed biological material is blood from within the peripheral vein; withdrawing and discarding the needle when the tip of the cannula is located properly within the peripheral vein; monitoring the status of the catheter tip within the peripheral vein from the cannula sensor: and generating an alert signal in the event the catheter tip begins to withdraw from the peripheral vein in order to shut off the infusate.

The sensors used can be a single type or multiple types that are capable of detecting impedance or resistive changes when the blood is sensed within the vein by an impedance drop. For instance, a suitable sensor type might include bio-impedance, micro electrodes for resonance impedance sensing of human blood as set forth in Sensors and Actuators A: Physical Volumes 146-148, July August 2008, Pages 29-36 and presented at the 14th International Conference on Solid State Sensors by authors Siyang Zheng, Mandheerej S. Nandra, Chi-Yuan Shih, Wei Li and Yu-Chong Tai in the Department of Electrical Engineering, California Institute of Technology, CA. USA, which paper is published by Elsevier and hereby incorporated by reference thereto. Other types of sensors that are capable of providing signals include medical Telesensor ASICs with detection of the blood reported back to the control panel by wireless telemetry. Very small medical Telesensor ASICS have been developed by Oak Ridge National Laboratory. The sensors might use technologies like magneto resistive, or micro-electro-mechanical systems (MEMES) sensors, acoustic sensors and others.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

This invention is explained in greater detail below in view of exemplary embodiments shown in the drawings, wherein.

DESCRIPTION OF PREFERRED EMBODIMENTS

Figure 1A:
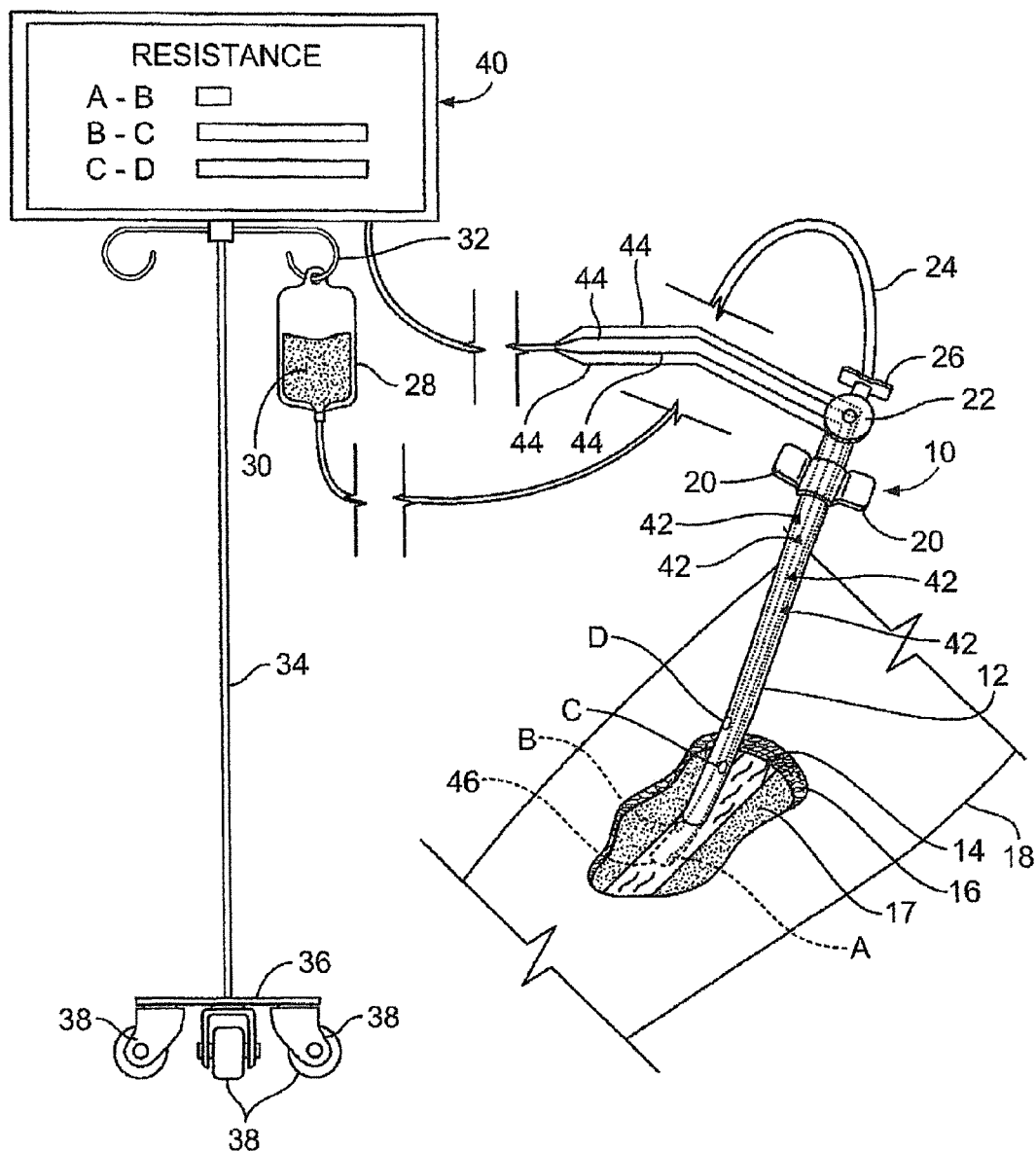
FIG. 1A shows a cannula with DC sensors made in accordance with the present invention completing a first stage insertion into a patient vein.
Figure 1B:
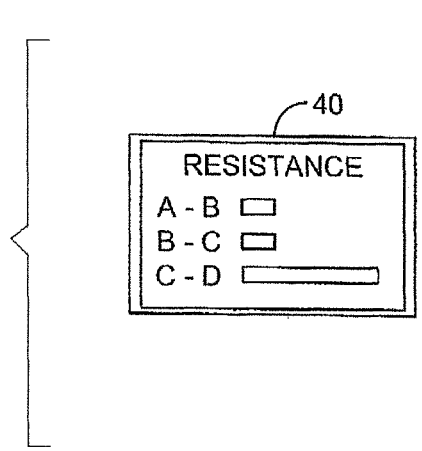
FIG. 1B shows a cannula with DC sensors made in accordance with the present invention completing a first stage and second stage insertion into a patient vein.
Figure 1B:
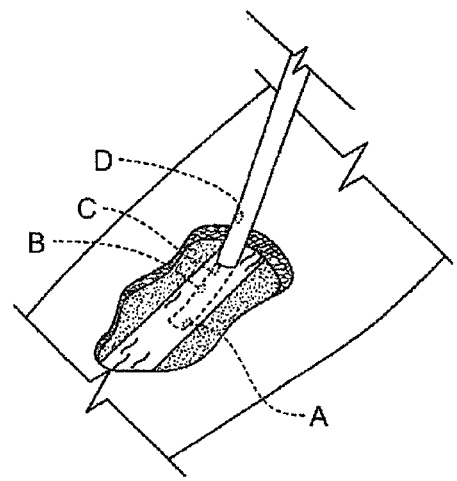
Figure 2A:
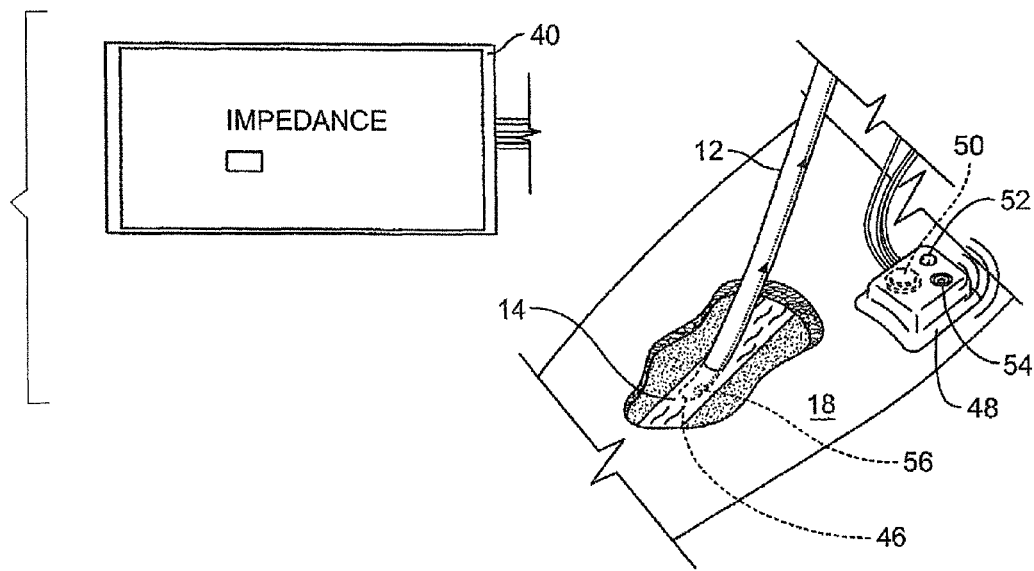
FIG. 2A shows a cannula with a single AC sensor made in accordance with the present invention sensing proper insertion of the cannula within the vein.
Figure 2B:
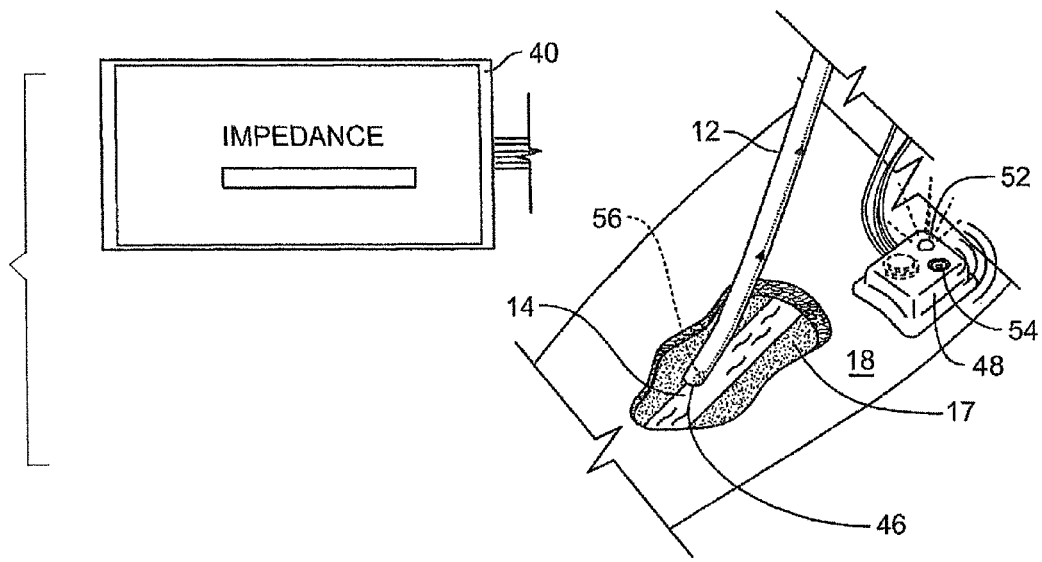
FIG. 2B shows a cannula with a single AC sensor made in accordance with the present invention sensing improper insertion of the cannula within the tissues surrounding the vein.
Figure 3A:
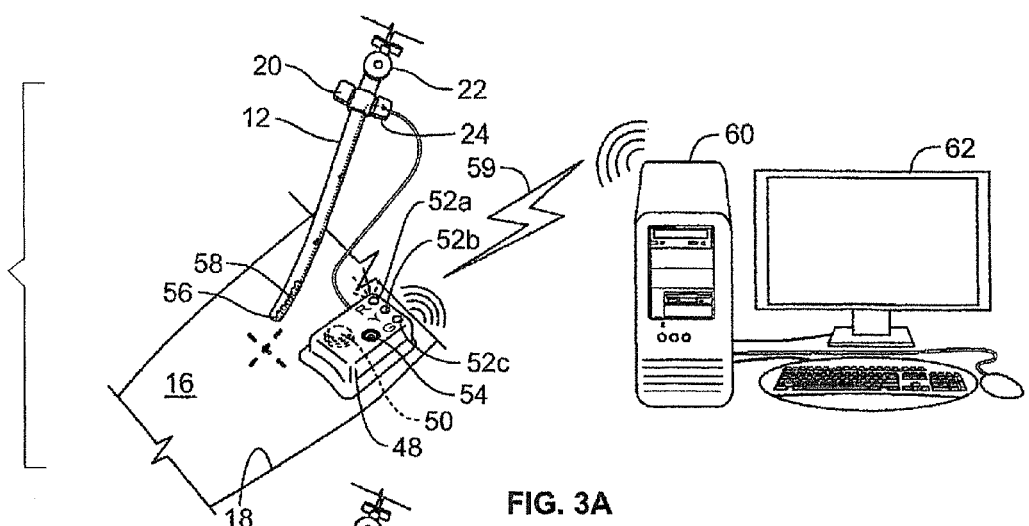
FIG. 3A shows a cannula with a single AC sensor and a conductive trace made in accordance with the present invention sensing a state prior to insertion within any vein.
Figure 3B:
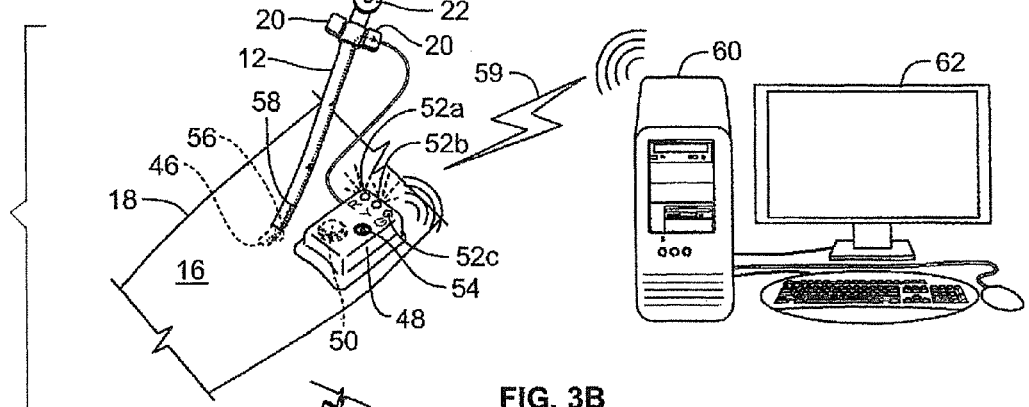
FIG. 3B shows a cannula with a single AC sensor and a conductive trace made in accordance with the present invention sensing insertion of the cannula into the tissues surrounding the vein.
Figure 3C:
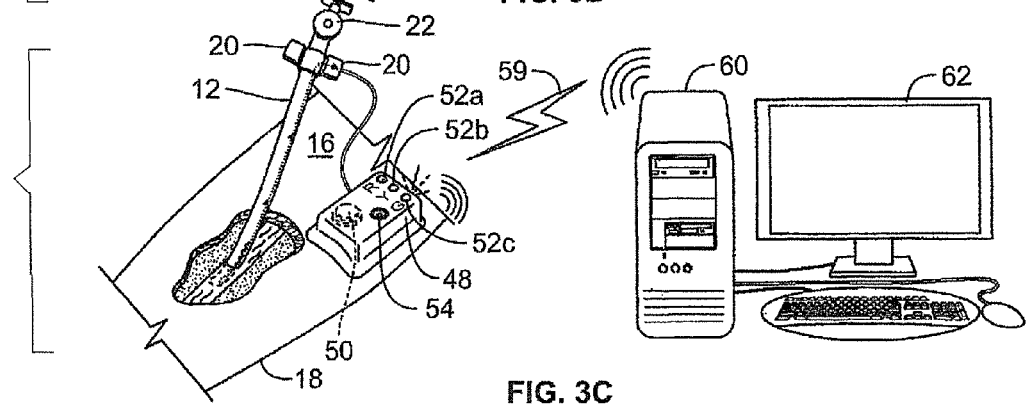
FIG. 3C shows a cannula with a single AC sensor and a conductive trace made in accordance with the present invention sensing proper insertion of the cannula into the vein.

The present invention relates to an intelligent intravenous apparatus and method for guiding and detecting proper insertion of a cannula tip of a catheter into a vein for infusion of intravenous (IV) fluids and further monitoring and sensing when a withdrawal of the cannula tip from the vein occurs. B. Braun Intrusion Safety IV Catheter is an example of a catheter that is capable of being modified to incorporate the features of the present invention. Various embodiments of the invention are contemplated. One embodiment is illustrated in FIGS. 1A-1D. A second embodiment is illustrated in FIGS. 2A and 2B. A third embodiment is illustrated in FIGS. 3A-3C. A fourth embodiment is illustrated in FIGS. 5A, 5B, 6, 7A, 7B and 8. In all illustrated embodiments, the cannula includes one or more sensors that provide signals indicating whether or not the cannula tip is properly inserted within a patient's vein or properly withdrawn therefrom to avoid medical complications with infusate. The broad principles of the invention are applicable to DC, AC and acoustical sensors with wires or wireless connections to electronic or electrical sensing module having signal processing and modulation electronics therein attached to the patient or connected by either a hardwired connection or wirelessly back to a control panel and/or base station that typical includes a computer with a monitor and keyboard.

As mentioned above, the first embodiment is illustrated in FIGS. 1A-1D and includes a catheter 10 constructed in accordance with the present invention. The typical catheter 10 consists of a short polymer tube (a few centimeters long) inserted through the skin into a peripheral vein 14 (any vein generally not inside the chest or abdomen). This is usually in the form of a flexible cannula 12 over-needle device, in which a flexible plastic cannula 12 comes mounted on a metal trocar (needle and trocar not shown as already withdrawn from cannula 12). Once the tip of the needle and cannula 12 are located within the vein 14 the trocar is withdrawn and discarded. The cannula 12 is further advanced inside the vein to an appropriate position and then secured with medical tape or the like over a pair of plastic wings 20 secured to the tubing near a port or hub 22. An IV line 24 connects to the port or hub 22 through a male fluid input 26 that is inserted into the IV line 24. The IV line 24 extends back to an IV Bag 28 containing the IV fluids 30. The IV Bag 28 is hung on a hook 32 on an IV Pole 34 held upright by an IV Pole Stand or Platform 36 having several wheel sets 38 attached thereto for portability of the IV Pole Stand 36.

Attached to the IV Pole 34 or Stand 36 or located at some other convenient place is a control and display panel 40. The control and display panel 40 includes a computer or microprocessor circuitry for processing input signals from the sensors and then displaying information related to insertion of the cannula through the skin and into a peripheral vein 14. Suitable circuitry adaptable to process the input signals is shown in the FIGS. 1, 4, 6 and 7 and taught in the specification of the U.S. Pat. No. 5,423,743 or is shown in FIGS. 1 and 2 and taught in the specification of the U.S. Pat. No. 4,959,050 and both are hereby incorporated by reference thereto. All of this circuitry is capable of being incorporated into a single micro integrated silicon chip or an application specific integrated chip (ASIC) in today's technology. Software required to program the ASIC and/or microprocessor circuitry is well known by a programmer of ordinary skill in the art of programming microprocessor and ASICS circuits. In fact, a person of ordinary skill in the art of programming is capable of writing numerous programs to provide the desired results set forth in this application. There are probably thousands of different ways to create a software program that is capable of processing the signals from the sensors and then generating a visual or audible alert to the end user of the apparatus and method in accordance with the present invention. For example, a simplified software programming would follow the logic diagrams and/or flowcharts as shown in FIGS. 4A-D to program the ASIC or microprocessor circuitry located in the monitor module 48 on the patient's forearm or back at the base station control panel 40. A micro-computer with appropriate inputs and outputs with a software program therein could duplicate some portion of the circuitry shown in '743 and '050 patents for electrical circuits capable of using either direct current ("DC") or alternating current ("AC") to power the guidance, monitoring and detection circuitry of the present invention. A Telesensor is capable of being used also. Medical telesensors are self-contained integrated circuits for measuring and transmitting vital signs over a distance of approximately 1-2 meters. The circuits of a Telesensor generally contain a sensor, signal processing and modulation electronics, a spread-spectrum transmitter, an antenna and a thin-film battery.

Turning now to FIGS. 1A-D, the cannula 12 of catheter 10 includes bio-impedance, micro electrode sensors or even telesensors A, B, C and D (hereinafter "sensors") embedded within the polymer or rubber during the manufacturing process of extruding the flexible plastic or rubber cannula 12 of the catheter 10. Thus in the preferred embodiment, the smart IV cannula 12 includes multiple (4-6) conductive spots exposed from the tip to the midpoint of the cannula 12, and each conductive spot includes conductive traces running back to the hub 22, and then either back to the control panel 40 or to a sensing monitor module 48 mounted by an adhesive backing on to the forearm 18 of the patient where the DC resistance and/or capacitance measurements are taken between the multiple spots or sensors A, B, C or D to determine whether the spots, and therefore the cannula 12, are in the vein 14 and bloodstream. This embodiment directly measures the conductivity within the bloodstream to determine cannula 12 position within it. The sensors or conductive spots A, B, C or D could also be mounted on the inner or outer surface of the cannula tubing 12 and then covered with a material bonded to the surface of the tubing 12. Also, as shown in FIGS. 1A-D, each sensor is connected by a hardwired line or conductive trace 44 indicated by an arrow 42 of any suitable conductor material to carry the extremely low level current and voltage of the microelectronic circuitry used to process the signals back to the control and display panel 40 at the base station or back to a monitor module 48 on the forearm 18 for processing of the input signals from the sensors.

As mentioned in the background of the invention, there are numerous scientific articles that discuss the ability to sense the conductivity of blood and thus its impedance. When the sensors or conductive spots A, B, C and D of the cannula 12 are in the top layers of skin 16 or within the subcutaneous tissues 17 surrounding the vein 14, the sensors would each generate a high impedance signal output back to the control panel 40 or module 48. In FIG. 1A, when the pairing of the sensors A and B ("first stage") are within the vein 14, the impedance would be indicated as being low on the control panel 40 at the base station. Meanwhile, when the pairings of the sensors B-C ("second stage") and C-D ("third stage") are still outside of the vein 14 and therefore not sensing the presence of the blood then a high impedance would be indicated back on the control panel 40 at the base station. Next, FIG. 1B shows the first and second stages sensing the presence of blood within the vein 14 and so the pairings of A-B and B-C would both show a low impedance detection.

Figure 1C:
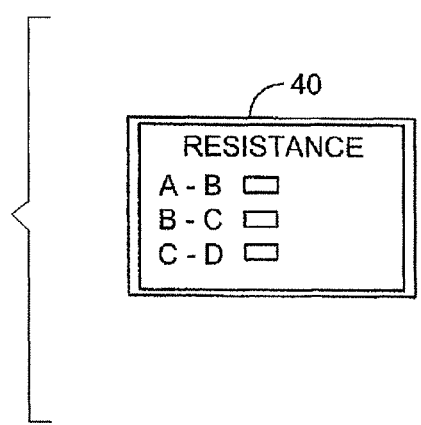
FIG. 1C shows a cannula with DC sensors made in accordance with the present invention sensing a first stage, second stage and third stage insertion into a patient vein.
Figure 1C:
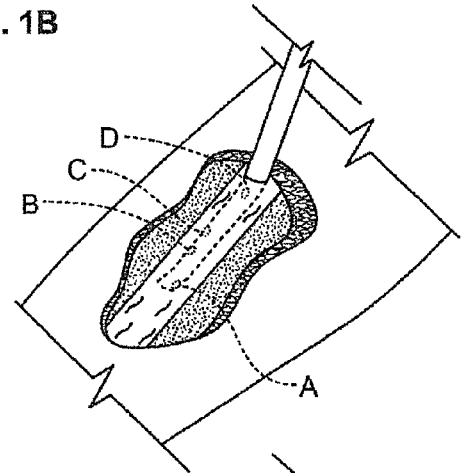
Figure 1D:
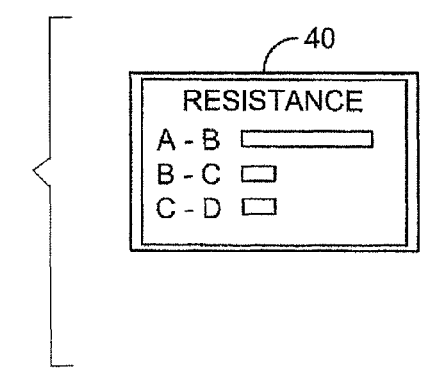
FIG. 1D shows a cannula with DC sensors made in accordance with the present invention sensing a second stage and third stage insertion into a patient vein with the first stage sensing the piercing of the vein wall and being outside of the vein into the surrounding tissues.
Figure 1D:
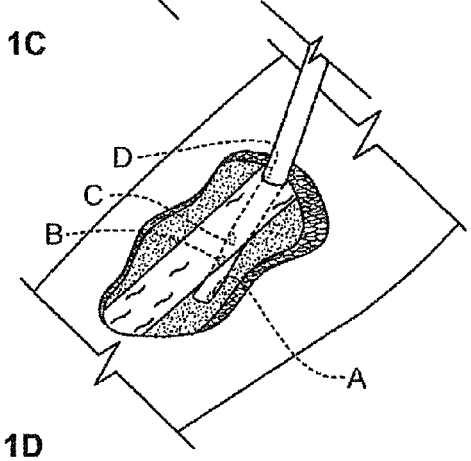

In FIG. 1C, all three stages or pairings of A-B, B-C and C-D are sensing the presence of blood so all three stages would show a low impedance on the control panel 40 indicating a proper insertion of the cannula 12 within the vein 14. If the medical technician pushed the cannula 12 through the vein 14 as shown in FIG. 1D then the first stage or pairing of sensors A-B would show a high impedance indicating that the distal end 46 of the cannula 12 had passed through the vein 14 and had gone back out into the subcutaneous surrounding tissue 17.

Turning now to FIG. 2A, an IV cannula with a single conductive spot or sensor 56 near the tip or distal end 46, with a conductive trace 44 running back to the hub 22, and thus to the sensing module 48 which is attached to the patient much like a conductive EEG pad. In this second embodiment, a 50 kHz signal (or other suitable AC freq) is transmitted and received through the cannula at a very low current of 500 μA and voltage by the sensing module 48. The signal impedance will vary significantly when the cannula 12 is in the vein/bloodstream vs insertion just under the skin 18 but not within the vein 14. The sensing module 48 further includes a soft switch or dome switch 50 to initiate the smart IV catheter when it is first taken from its package. Or the sensing module 48 is initiated when the adhesive cover is removed when the catheter is taken out of its packaging and placed onto the forearm 18. There is also an LED 52 and audible piezo horn 54 mounted within the sensing module 48 for providing guidance signals for the proper insertion of the cannula 12 within the vein 14. This makes the apparatus 10 of the present invention totally portable for EMT usage in the field. The sensing module 48 mounted on the forearm 18 of the patient further includes a battery power source to run the circuitry. Because the sensor 56 is within the vein 14, a low impedance visual signal from the LED 52 and/or an audible sound corresponding to low impedance visual alert would be given by the piezo horn 54.

FIG. 2B shows the cannula 12 inserted below the top surface of the skin 16 but not within the vein 14 so the impedance reading would be high as indicated on the monitor panel 40 and a corresponding color on the single LED 52 would blink or provide a steady red or flashing yellow color along with the audible signal from the horn 54 corresponding to the LED pattern of colors.

FIGS. 3A-C shows a third embodiment which is another version of the second embodiment but further includes wireless transmission by either Bluetooth or WiFi 59 to a computer base station 60 in which the conductive spot or sensor 56 at the tip of the cannula 12 is followed by an exposed, partially conductive trace 58 extending toward the hub 22 for about a centimeter or more on the cannula 12. This will increase the resolution of the signal measurement when the cannula tip 46 is either pushed through the vein, or has begun to withdraw from the vein. This embodiment is a wireless version of either the AC or DC circuitry previously described. The computer base station 60 would allow for a more sophisticated programming of the overall systems incorporating the smart IV catheter for guiding the medical professional when inserting the cannula within a vein 14 of the patient. For example, partially conductive trace would allow a variation of colors to be used with the LED visual indication of the progress being made by the medical professional. The colors of red 52a, yellow 52b and green 52c are shown on the sensing module 48 but other colors might be used too when using the computer 60 with a monitor 62 allowing the use of many different colors to match the stage of progress during the insertion of the cannula tubing 12 within the forearm and guiding inside of the vein 14.

For example, in FIG. 3A the cannula tubing 12 is above the skin 16 so a red LED 52a is visually displayed on the sensing module 48 and then on the computer monitor or screen 62. FIG. 3B shows a partial insertion and the colors of red 52a and yellow 52b may be visible by the LEDs on the sensing module 48 and on the computer monitor 62. Finally, in FIG. 3C, the cannula 12 is properly inserted within the vein 14 and the steady color of a green LED 52c is visible on the sensing module 48 and then likewise on the computer monitor 62.

For the second and third embodiments, the smart IV catheter of the present invention uses bioelectric impedance to monitor infiltration using a 50 KHz signal at 500 μA. This high frequency signal at low amperages is similar to handheld AC devices made by Tanita and Omron Corporation in U.S. Pat. No. 7,039,458 and U.S. RE 37954 that operate somewhat similar but are totally different in functioning and method.

FIGS. 4A-D shows simple flowcharts for the operation of the smart IV catheter. Turning now to 4A, when a portable catheter 10 made in accordance with the invention is taken out of its packaging with the attached sensing module 48, the user removes the adhesive backing cover, which turns on the power and initializes the circuitry of the module 48. Alternatively, the soft button 50 is pushed to power on/initialize the device. First, the DC version of embodiment of the device first checks the three stages and the sensors thereof to make sure the impedance is high for all three pairings of sensors. The LEDs preferably flash in a sequence of green, yellow and red to indicate a good device. Optionally, the piezo horn provides three short tones to indicate that the catheter is not functioning properly. In the AC version, a check of the impedance cannula emitter (TX) to base (RX) is done which should show a high impedance when initialized.

Figure 4A:
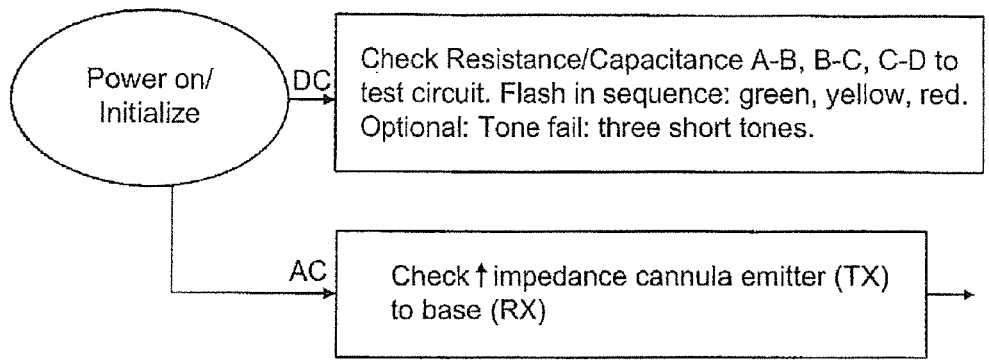
FIG. 4A shows a flowchart where the cannula and circuitry are initialized.
Figure 4B:
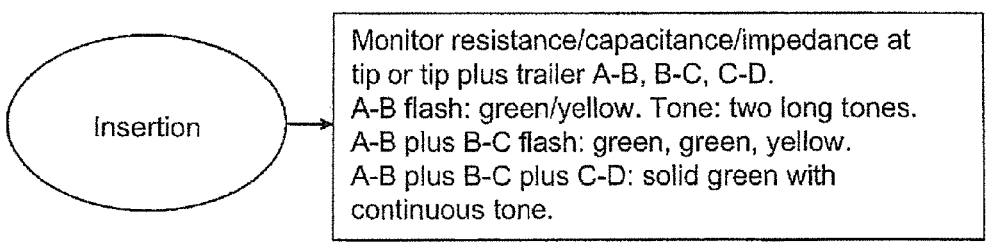
FIG. 4B shows a flowchart where the sensors of the cannula are at various stages during insertion into a peripheral vein of a patient in accordance with the invention of FIG. 1A.

FIG. 4B show the steps when insertion is being done by the medical professional. There is a monitoring resistance/capacitance/impedance at tip or tip plus trailer A-B, B-C and C-D. A-B flashes green/yellow LED colors and a tone of two long tones is emitted. If there is A-B plus B-C then the LEDs flash green, green and yellow. And finally, if there is A-B, plus B-C, plus C-D flash solid green with a continuous tone for a predetermined count and then stop to preserve the battery.

Figure 4C:
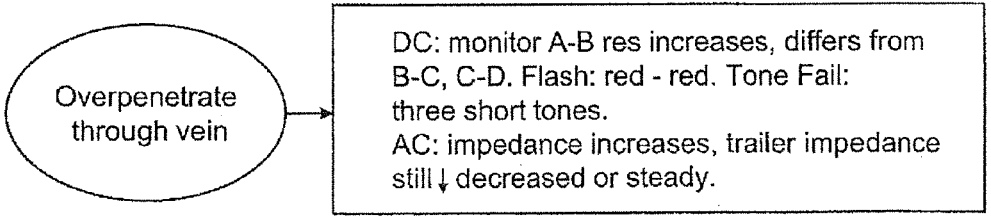
FIG. 4C shows a flowchart where the sensors of the cannula indicate an over penetrate through the vein in accordance with the invention of FIG. 1A.

FIG. 4C shows an overpenetration through the vein. In the DC version of the device, the A-B resistance increases as it passes through the vein and the B-C and C-D stages continue indicating a low impedance. The device then creates an alert to the medical professional with the LED flashing red-red and an audible tone indicating failure occurs so that IV fluids may be stopped. In the AC version, the spot or sensor at the tip increases in impedance while the trailer conductive strip is still decreasing or is steady.

Figure 4D:
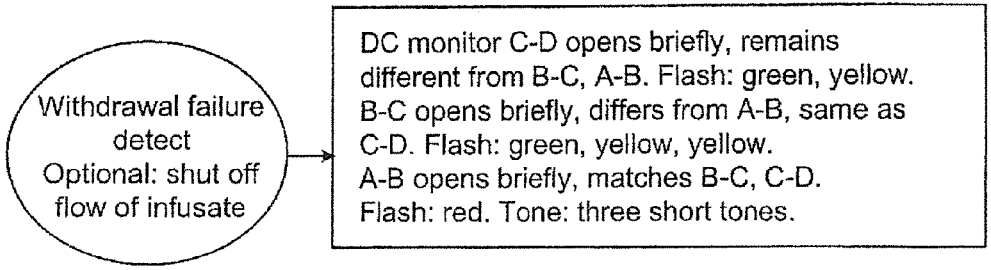
FIG. 4D shows a flowchart where the sensors of the cannula indicate withdrawal failure detection and shut off flow of infusate in accordance with the invention of FIG. 1A.

In the final flowchart, FIG. 4D deals with the situation when there is a withdrawal failure detected and a shut off of the infusate needs to be initiated. Here as the cannula pulls out of the vein, in the DC version the last stage C-D opens briefly and remains different from B-C and A-B. An LED display of green, yellow occurs. Then as B-C opens briefly, it will differ from A-B and flashes similar to C-D with a flash of green, yellow and yellow. And then when A-B opens briefly, it matches B-C and C-D. Then the alert on the display becomes a solid red color on the LED while three short audible tones are repeated indicating a failure has occurred with the withdrawal of the cannula tip from the vein.

Figure 5A:
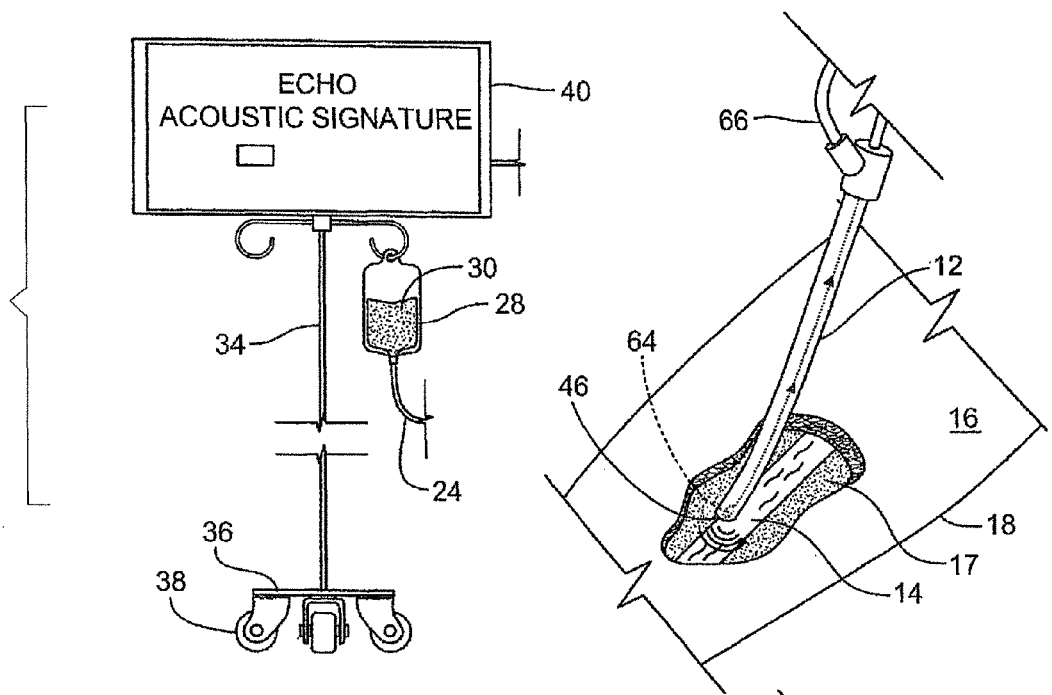
FIG. 5A shows a cannula with an acoustical sensor made in accordance with the present invention prior to proper insertion within the vein in accordance with the present invention of FIG. 1A.
Figure 5B:
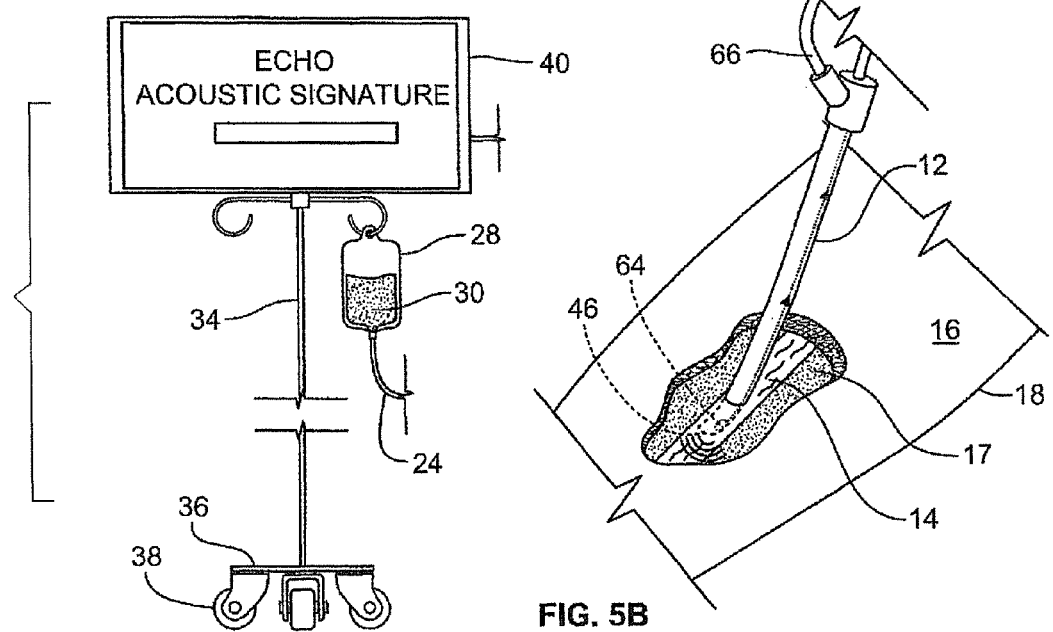
FIG. 5B shows a cannula with an acoustical sensor made in accordance with the present invention with proper vein insertion in accordance with the present invention of FIG. 1A.

In FIGS. 5A-B, a fourth embodiment shows the use of an acoustical signature for the apparatus and method to continuously monitor that the cannula 12 is remaining properly inserted within the vein 14 in accordance with the present invention. The cannula 12 includes an acoustical transducer 64 of a broadband 25 to 50 MHz type well known in the art such as the medical transducers manufactured and sold by General Electric Company of Schenectady, N.Y. The transducer 64 is placed at a position along the cannula 12, such as near the tip 46 of the cannula 12, within or on a hub 22 at an end opposite the tip 46, or in or on the cannula in between the tip 46 and the hub 22, such that a large amplitude echo signal from the transducer 64, 64' is continuously monitored to indicate the correct tip placement of the cannula tubing 12 within the vein 14. In one embodiment of this invention, the transducer 64, 64' is angled with respect to the cannula 12 in an insertion direction, such as having an emitting and/or receiving sensor component or surface disposed at 45-90° relative to the longitudinal axis of the cannula 12.

As shown and described, transducer 64, 64' may be positioned within the cannula 12 as shown in transducer 64 or, alternatively, upstream of and external to the cannula 12 such as shown in transducer 64'. In one embodiment, the transducer 64, 64' is positioned upstream from the tip 46 so that the transducer 64, 64' is not beneath the skin 16 upon insertion of the tip 46, and can be placed in the upper 75%, desirably the upper 50%, and preferably the upper 25% of the cannula 12. In one preferred embodiment, the transducer 64, 64' is placed at, either on or within, the connecting hub 22. As such, transducers 64, 64' shown in FIG. 5A are intended to show two alternative feasible placements for use in the subject system. If suddenly a smaller amplitude echo signal from the transducer 64, 64' is detected then this provides an indication that the tip of the cannula 12 of the catheter 10 is withdrawing from the vein 14 into the subcutaneous tissue surrounding the vein.

Most high frequency transducers for medical applications are made from a thin piezo-electric polymer film. The transducing element 64, 64' is mounted within the cross section near the cannula tip 46 or upstream of the cannula tip 46, respectively. A coaxial cable 66 within the cross section of polymer cannula 12 connects the transducer to an external signal source. Electrical signals are transmitted to and received from the ultrasonic transducer 64, 64' via the coaxial cable running the length of the cannula and out the hub area 22 back to either the signal processor in the sensing module 48 or the base station control panel 40. The external signal source for the ultrasonic transducer is well known in the art. The control panel screen or the LED(s) on the sensing module 48 provides a display for the received transducer signals to monitor the placement of the tip 46 of the cannula within the vein 14.

FIG. 5A further shows that the cannula is through the outer surface of the skin 16 but not yet within the vein 14 so the acoustical signature echo generated is small in amplitude due to the dense nature of the normal tissues rather than a greater amplitude echo signature when the transducer 64, 64 is within a bloodstream of the vein 14. On the other hand, FIG. 5B shows the cannula 12 and within the vein 14 and the echo signature picked up from the distal end 46 of the cannula tubing 12 is generating a larger amplitude echo signal for indicating that the tip of the cannula tubing 12 is properly secured within the bloodstream of the vein 14. The magnitude of the echo signature is then either displayed on the screen of the control panel 40 or indicated by visual and/or audible sounds on the sensing module 48. In summary, when the cannula 12 is outside of the vein 14, the amplitude echo signal generated by the transducer is small and when the cannula 12 is within the vein and sensing the bloodstream, the echo signal is large.

Figure 6:
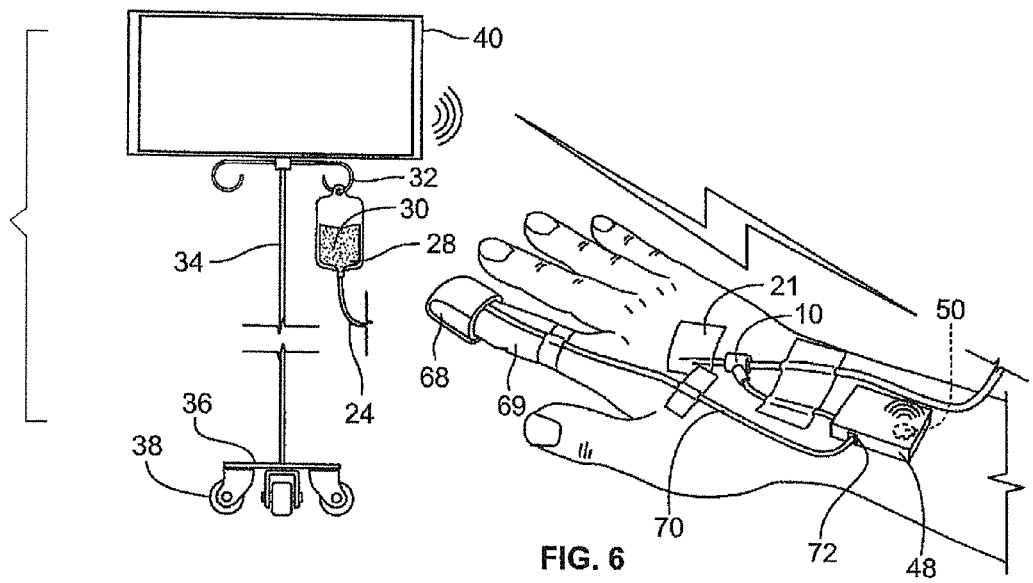
FIG. 6 shows a cannula with an acoustical sensor made in accordance with the present invention with proper vein insertion including other monitoring devices connected to the processing module which wirelessly transmits signals to a base station display in accordance with the present invention of FIG. 1A.

In FIG. 6, the cannula 12 is properly inserted within the vein 14 with the acoustical signature being used with a sensing module 48. Also, a pulse oximeter 68 which is a non-invasive method allowing the monitoring of the oxygenation of a patient's hemoglobin is connected to the index finger 69 and its output signal is connected via a conductor 70 to an input terminal 72 to the sensing module 48. Moreover, the sensing module 48 might have other inputs such a blood pressure monitoring input. The unique feature also shows that the sensing module 48 is sending back its signal of the smart IV catheter 10 insertion plus information from the pulse oximeter 68 wirelessly to the base station control and display panel 40.

Figure 7A:
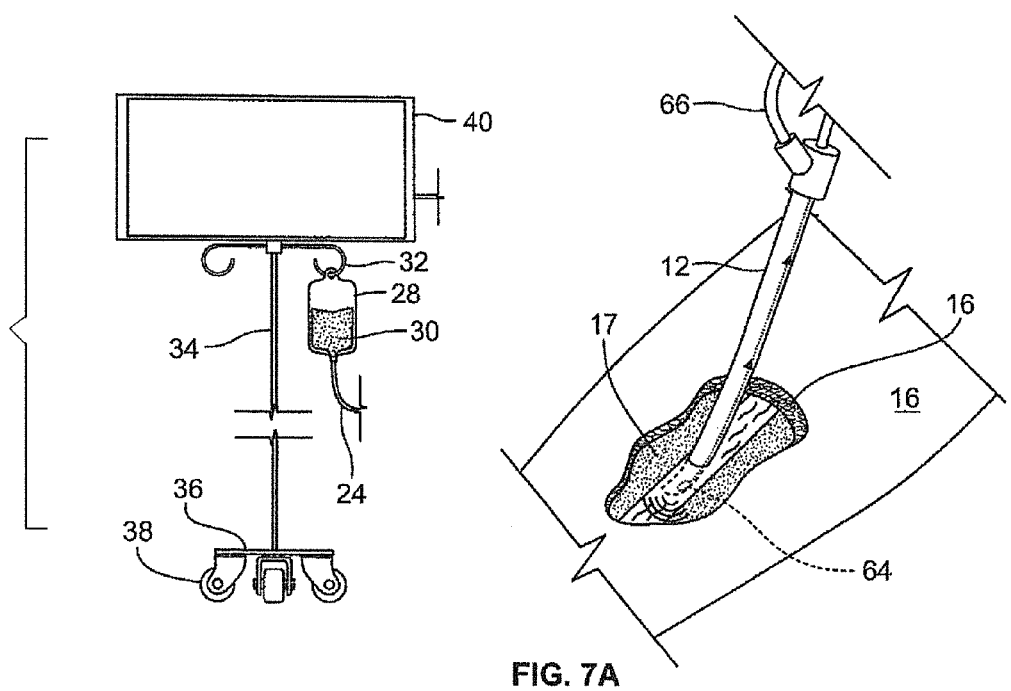
FIG. 7A shows a cannula with an acoustical sensor made in accordance with the present invention with proper vein insertion hardwired to a control panel and/or base station for processing and monitoring the vein insertion in accordance with the present invention of FIG. 1A.
Figure 7B:
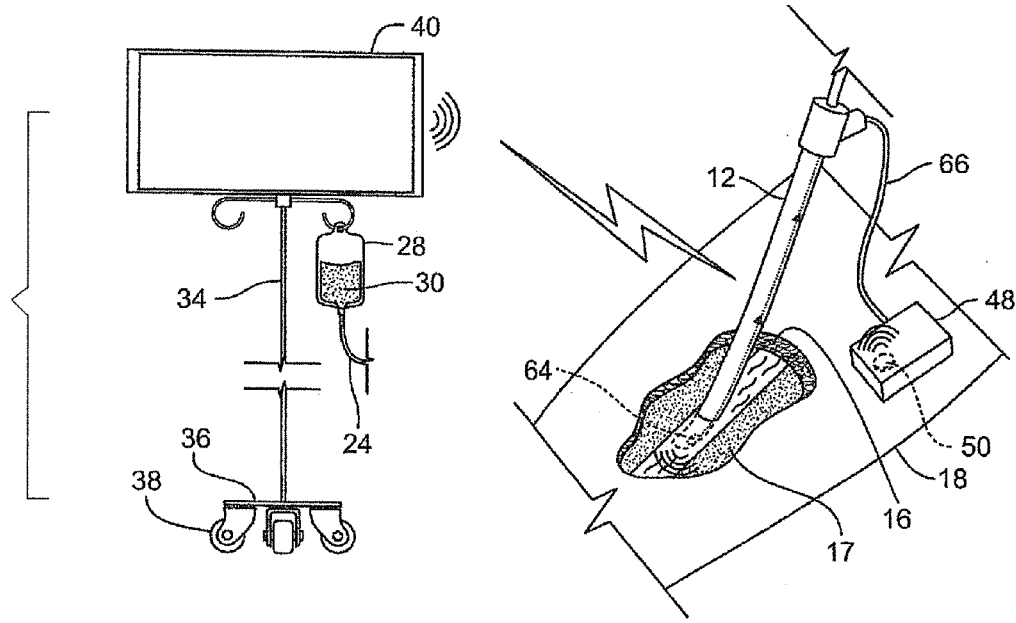
FIG. 7B shows a cannula with an acoustical sensor made in accordance with the present invention with proper vein insertion wirelessly sending the sensing signals to a control panel and/or base station for processing and display in accordance with the present invention of FIG. 1A.

FIG. 7A shows an acoustical signature device that includes a hardwire connection back to the control and display panel 40. FIG. 7B shows an acoustical signature device that includes a wireless transmission back to the control and display panel 40. Both devices as shown in FIGS. 7A-B function as previously described for the devices shown in FIGS. 5A-B above for the apparatus and method in accordance with the present invention.

According to the embodiments shown in FIGS. 5-7, IV infiltration occurs when the cannula 12 pulls out of the vein yet remains under the skin. The embodiments shown in FIGS. 5-7 may further detect and identify occlusions as described below. Occlusion occurs when the cannula 12 remains in the vein, properly placed, but starts to accrete blood platelets at the orifice of the tip. This blood clot accretion at the orifice of the tip slowly closes off the tip to any fluid flow. When this occurs, the medical professional often has to pull The IV and run a new one, an expensive and often painful inconvenience. Medical professionals have to watch for occlusion indications and keep the cannula 12 open by pushing saline through the cannula or Heparin, an anticoagulant.

According to a preferred embodiment, the sensing module 48 and/or the display module 40 may be tuned in such a way as to detect a reduction in return echo strength from the acoustical transducer 64, 64, so as to detect occlusion in process before it fully closes the tip of the cannula 12. With a desired acoustical transducer 64, 64' and software analysis capability, movement of the cannula 12 within the vein (termed a "trombone effect") and occlusion of the tip of the cannula 12 may be sensed and detected.

Figure 8:
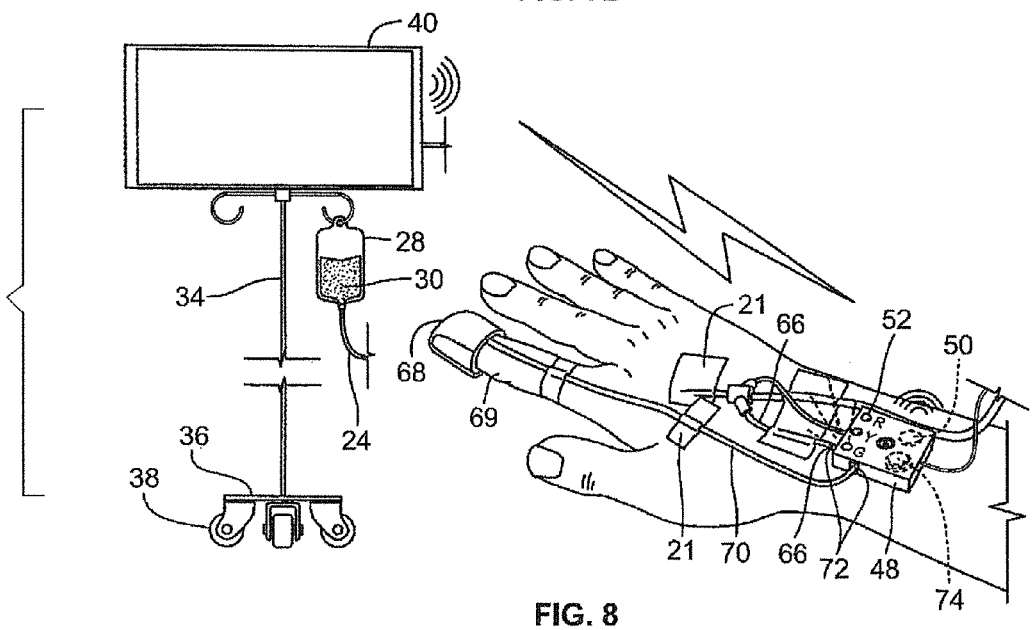
FIG. 8 shows a cannula with an acoustical sensor made in accordance with the present invention with proper vein insertion including other monitoring devices connected to the processing module which wirelessly transmits sensor and other device signals to a base station for processing and display in accordance with the present invention of FIG. 1A.

FIG. 8 shows the wireless connection back to control panel 40 in which the pulse oximeter 68 is connected from the index finger 69 back to the sensing module 48 and further may include a blood pressure input to the sensing module 48 (not shown). In addition, the sensing module further includes a reflective pulse oximeter 74 mounted within the sensing module 48 that shines down into the hand from the backside of the sensing module 48 for its measurements, includes bright red, yellow and green LED lights to show the various stages of operation of the device covered by the apparatus and method claims.

As noted above, the present invention is directed generally to a medical device and more particularly to an electrical signal-guided catheter with sensors embedded in the polymer skin of a flexible plastic cannula to sense the presence of the bloodstream for proper insertion of the cannula tubing within a peripheral vein to administer IV fluids. The electrical signals corresponding to the sensing of subcutaneous tissue and the bloodstream within a vein provide an electronic signal visualization of the placement through the skin and subcutaneous tissues into the vein and further including a method to locate the flexible cannula within the vein for correct catheterization. Secondly, this catheter detects any improper withdrawal of the catheter from the vein and thus a leakage into the subcutaneous tissues indicating an infiltration condition.

According to one preferred embodiment of this invention, the smart IV cannula 12 as shown and described may further include a superhydrophobic coating and/or construction. Accordingly, the cannula 12 may include at least one of: a micro- or nano-coating over and/or within the cannula 12; the cannula 12 may be constructed or Teflon® or silicone; and/or a hybrid construction, such as silicone oil impregnated urethane.

A suitable micro- or nano-coating may comprise a coating such as described in U.S. Pat. Nos. 8,574,704 and 8,535,779 to Smith et al., which are hereby incorporated by reference. The Smith et al. patents describe non-wetting surfaces that include a liquid impregnated within a matrix of micro-/nano-engineered features on the surface, or a liquid filling pores or other tiny wells on the surface. Such a product, called Liquiglide™, may be used to coat the cannula 12 described herein. As described, a micro/nano-engineered surface coating enables a durable liquid-impregnated surface coating to be placed over the full exterior and interior surfaces of an IV cannula 12.

Alternatively, the cannula 12 may be constructed of a non-stick material such as Teflon® or silicone. The cannula 12 may be wholly constructed of such material or partially constructed, coated and/or reinforced with such material.

According to another alternative of the subject invention, the cannula 12 may comprise a hybrid construction that includes a hydrophobic coating impregnated within or coated over and around a non-stick construction. Such, hybrid construction may include a silicone oil impregnated urethane construction.

A benefit of such liquid-impregnated surface coating or alternatively described constructions is to inhibit the initial "seed" adhesion of blood protein fibrin to the cannula surface, thus preventing further fibrin accretion at the orifice of the tip of the cannula, thus preventing IV cannula occlusion.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

What is claimed is:

1. An intravenous catheter for guiding tip placement into a peripheral vein, comprising:
    a flexible, tubular cannula including an insertion tip that is insertable into a peripheral vein;
    an sensor mounted external of the cannula for sensing and then generating an output signal representative of a sensed biological material including blood at the insertion tip of the cannula, wherein the sensor is mounted at a hub adapted to attach the cannula to an IV bag and the sensor comprises an acoustical transducer;
    a processor circuitry connected to the sensor output signal for receiving and then generating a display; and
    wherein the display provides a feedback to a medical personnel of insertion tip placement during transition into, placement within, and withdrawal from the peripheral vein of a patient body, wherein the feedback comprises a first signal during skin penetration, a second and different signal after skin penetration, and a third and further different signal upon the proper insertion of the cannula within the peripheral vein.

2. The invention of claim 1, wherein the sensor generates an amplitude echo signature signal within the cannula when energized.

3. The invention of claim 1, wherein the sensor is embedded at an angle to a longitudinal axis of the cannula.

4. The invention of claim 3, wherein the sensor comprises a piezo-electric polymer film sensor.

5. The invention of claim 1, wherein the predetermined location is outside the vein when the cannula tip is inserted.

6. The invention of claim 1, further comprising a cable embedded within the hub of the cannula and connecting the sensor to the processor circuitry.

7. The invention of claim 1, wherein the processor circuitry is connected to the sensor at the hub.

8. The invention of claim 1, further comprising a different color light signal for each of the first signal, the second signal, and the third signal.

9. The invention of claim 1, wherein the cannula comprises a liquid impregnated surface.

10. The invention of claim 1, further comprising a hydrophobic micro-coating or nano-coating coating the cannula.

11. The invention of claim 1, wherein the sensor is a telesensor for wirelessly transmitting and receiving signals from the processing circuitry.

12. The invention of claim 1, further comprising an LED display corresponding to the sensed biological material in the body.

13. An intravenous catheter for guiding tip placement into a peripheral vein and monitoring the tip removal from the peripheral vein, comprising:
    a flexible plastic, tubular cannula having a tip at a distal end for insertion into a peripheral vein of a body and a hub at the opposite end for attachment to an IV bag including an infusate;
    a sensor mounted external of the cannula and at the hub for sensing the impedance of a sensed biological material in the body including the blood and then generating an output signal representative of a sensed biological material, wherein the sensor comprises an acoustical transducer that generates an amplitude echo signature signal when energized; and
    processor and modulation circuitry connected to the output signal and that receives and then generates one of at least three different feedback signals as a display or audible sound representing the location of the cannula tip within the biological material being sensed in the body during insertion of the cannula or upon the withdrawal of the cannula from the body, wherein the feedback signals comprise a first signal during skin penetration, a second and different signal after skin penetration, and a third and further different signal upon the proper insertion of the cannula within the peripheral vein.

14. The invention of claim 13, wherein the display provides a feedback to a medical personnel upon correct catheter tip placement in the peripheral vein of the patient and wherein the display or audible sound provides an alert to shut off the infusate when the tip dislodges from the vein but remains in the body to avoid infiltration into the subcutaneous tissues of the body.

15. The invention of claim 13, wherein further including a sensing module housing the processor and modulation circuitry having an adhesive backing for attachment to the skin of the body in near proximity to the catheter.

16. The invention of claim 15, wherein the sensing module further includes Bluetooth or WiFi circuitry for wirelessly communicating to a base station control and display panel for assisting in the insertion of the catheter tip in the vein and then subsequently monitoring the tip within the vein to detect a withdrawal of the tip from the vein.

17. The invention of claim 15, further including a pulse oximeter connected to the index finger having an output signal connected to an input port on the sensing module, and/or a reflective pulse oximeter on the adhesive backside for measuring the oxygenation of the hemoglobin in a bloodstream within the vein.

18. A method of inserting and monitoring the placement of a catheter within a peripheral vein on a patient body, the method comprising:

inserting a cannula-over-needle apparatus into the body, the apparatus including a cannula connected to an IV bag at a hub opposite a cannula tip;

sensing various biological material within the body from detection circuitry connected to a sensor mounted external of the cannula and at the hub, wherein the sensor is an acoustical transducer generating an amplitude echo signature signal when energized;

guiding the cannula tip corresponding to the sensed biological material in the body;

stopping the insertion of the cannula into the body upon receiving a proper insertion signal when the sensed biological material is blood from the interior of the peripheral vein;

withdrawing and discarding the needle when the cannula tip is located properly within the interior wall of the peripheral vein;

monitoring the status of the cannula tip within the peripheral vein from the cannula sensor; and generating an alert signal in the event the cannula tip begins to withdraw from the peripheral vein in order to shut off an infusate wherein the insertion signal and the alert signal are two of at least three unique signals generated by the detection circuitry, wherein the three unique signals comprise a first signal during skin penetration, a second and different signal after skin penetration, and the insertion signal being a third and further different signal upon the proper insertion of the cannula within the peripheral vein.

\* \* \* \* \*